United States Patent
Hermentin et al.

[11] Patent Number: 5,095,097
[45] Date of Patent: Mar. 10, 1992

[54] MAGNETIC PROTEIN CONJUGATES, A PROCESS FOR THE PREPARATION THEREOF AND THE USE THEREOF

[75] Inventors: Peter Hermentin, Marburg; Reiner Dönges, Gladenbach; Udo Franssen, Marburg; Karlheinz Enssle, Marburg; Heinz-Jürgen Friesen, Marburg, all of Fed. Rep. of Germany

[73] Assignee: Behringwerke Aktiengesellschaft, Marburg, Fed. Rep. of Germany

[21] Appl. No.: 538,753

[22] Filed: Jun. 15, 1990

[30] Foreign Application Priority Data

Jun. 19, 1989 [DE] Fed. Rep. of Germany ....... 3919873

[51] Int. Cl.$^5$ ...................... C07K 17/02; C07K 15/28; C12N 11/06
[52] U.S. Cl. .................... 530/391.5; 530/404; 530/405; 530/408; 530/409; 435/2; 435/174; 435/188; 436/526
[58] Field of Search ............... 530/390, 391, 388, 408, 530/409, 404, 405; 435/2, 174, 188; 436/526

[56] References Cited

U.S. PATENT DOCUMENTS

| | | | |
|---|---|---|---|
| 4,241,176 | 12/1980 | Aurameas et al. | 435/7 |
| 4,671,958 | 6/1987 | Rodwell et al. | 424/85.01 |
| 4,698,302 | 10/1987 | Whitehead et al. | 435/94 |
| 4,795,698 | 1/1989 | Owen et al. | 435/4 |
| 4,814,098 | 3/1989 | Inada et al. | 252/62.51 |

FOREIGN PATENT DOCUMENTS 0125995 11/1984 European Pat. Off.
WO83/03920 11/1983 PCT Int'l Appl.

OTHER PUBLICATIONS

Treleaven et al., The Lancet, 1, No. 8368, 70-73 (1984).

Hermentin et al., Bioconjugate Chem., 1, 411-418 (1990).

"Elimination of B-Lymphoma Cells From Human Bone Marrow: Model Experiments Using Monodisperse Magnetic Particles Coated with Primary Monoclonal Antibodies", G. Kvalheim et al., Cancer Research, 47, 846-851, 2/87.

"Depletion of T Lymphoctyes From Human Bone Marrow", F. Vartdal, Transplantation, vol. 43, No. 3, 366-371.

"Isolation of Lymphocytes, Granulocytes and Macrophages", A. Boyum, Scand. J. Immunol., vol. 5, Suppl. 5, 1976, pp. 9-15.

"A Method for the Preparation of Protein-Protein Conjugates of Predermined Composition", Journal of Immunological Methods, 24 (1978), 321-336, Rector et al. Blair et al. (1983) J. Immunol. Methods 59:129-143.

Primary Examiner—Christine Nucker
Assistant Examiner—Kay K. Kim
Attorney, Agent, or Firm—Finnegan, Henderson, Farabow, Garrett and Dunner

[57] ABSTRACT

The invention relates to magnetic protein conjugates of the formula I $$M-NH-CO-(CH_2)_n-S-P' \qquad I$$

with n=1-6, preferably with n=1 or 2 and particularly preferably with n=1, in which M is a dispersible, magnetically reacting material or particle which carries amino groups, and P' is a protein, to a process for the preparation thereof and to the use thereof for the specific removal of cells or soluble antigens, receptors, substrates, cofactors or carbohydrate determinants from aqueous salt solutions or body fluids or as part of a diagnostic method or as a diagnostic aid, preferably for the removal of cells, preferably for bone marrow depletion or for HLA typing.

15 Claims, No Drawings

MAGNETIC PROTEIN CONJUGATES, A PROCESS FOR THE PREPARATION THEREOF AND THE USE THEREOF

The invention relates to magnetic protein conjugates of the formula I $$M-NH-CO-(CH_2)_n-S-P' \qquad I$$

with n=1–6, preferably with n=1 or 2 and particularly preferably with n=1, to which the following applies:

M is a dispersible, magnetically reacting material or particle which carries amino groups, and P' is a protein.

P' can be a protein in which one or more sulfhydryl groups are either present in the natural way or generated by reduction of disulfide linkages or introduced by chemical reaction.

P' is, in particular, an immunoglobulin or immunoglobulin residue, preferably a monoclonal antibody or a Fab, Fab' or F(ab')$_2$ fragment, an antigen or a residue of an enzyme, hormone, lectin or growth factor.

P' is preferably a monoclonal antibody of the IgG or IgM class, in particular a monoclonal antibody which is directed against an antigen which is present in dissolved form in body fluids or aqueous salt solutions or a monoclonal antibody which is directed against an antigen which is expressed on cells, in which case the cells expressing the antigen can be, in particular, cells of the myeloid or lymphatic system, cells of the peripheral blood, especially B lymphocytes, T lymphocytes or precursor cells thereof, or tumor cells, especially tumor cells of the bone marrow. These cells can also be erythrocytes, bacteria, mycoplasmas or protozoa. However, viruses are also to be regarded as cells within the scope of the invention.

M is preferably a dispersible particle with a metal oxide core and an enveloping coat carrying amino groups, it being possible for a group of paramagnetic substances to be embedded in the metal oxide core, preferably a particle whose diameter is between about 0.1 μ and about 100 μ, but preferably between about 0.1 μ and about 1.5 μ.

The invention furthermore relates to a process for the preparation of a magnetic protein conjugate of the formula I and to the use of a conjugate of the formula I for the specific removal of cells or soluble antigens, receptors, substrates, cofactors or carbohydrate determinants from aqueous salt solutions or body fluids, and to the use as part of a diagnostic aid or as a diagnostic aid, and, in particular, to the use for bone marrow depletion or for HLA typing.

A bone marrow transplantation is often the only therapeutic option, inter alia in the treatment of certain types of leukemia and of panmyelopathy (myelophthisis).

Patients with leukemias and certain lymphoid neoplasms are occasionally subjected to whole-body irradiation with an extremely high dose and/or aggressive chemotherapy. Treatment of this type entails complete destruction of the normal stem cells of the bone marrow, the precursors of all blood cells. The patient therefore receives reinfusion of bone marrow from a suitable donor, from which cells colonize the bone marrow cavities of the recipient and thus make it possible for the hemopoietic and immune system to develop anew. This method is called allogenic bone marrow transplantation.

The T lymphocytes of the donor which are transferred with the reinfused bone marrow into the patient and which recognize the cells of the recipient as foreign, and therefore attack and destroy them, are responsible, inter alia, for the high risk associated with allogenic bone marrow transplantation. This bone marrow intolerance, which is often life-threatening for the patient, is called the graft-versus-host reaction or graft-versus-host disease (GVHD). The risks associated with this graft-versus-host disease can be reduced, on the one hand, by the patient being reinfused, where possible, with accurately typed bone marrow from particularly suitable donors, usually from among relatives. However, on the other hand, they can also be reduced by selective elimination of undesired cell populations as may be represented by, for example, T lymphocytes in the donor's bone marrow before reinfusion into the patient. This elimination of donor's T cells can be carried out, for example, by selective lysis of the cells which are to be removed in the presence of complement or by selective killing of the T cells using so-called immunotoxins or by another method, for example by magnetic cell depletion of the bone marrow.

Bone marrow cell depletion of this type can be carried out in a relatively straightforward manner by incubating the bone marrow with a murine monoclonal antibody which is, for example, directed specifically against the T cells of the bone marrow and, as a consequence, binds only to the T cells. Such T cells loaded with murine monoclonal antibodies can now be removed in a second step by incubating them, for example, with rabbit anti-mouse immunoglobulin which is bound to magnetic particles, which results in the T lymphocytes being loaded in a specific manner with the magnetic material so that they can be removed from the bone marrow using a magnet (see in this connection Vartdal et al., Transplantation (1987), 43, 366–371 and the literature cited therein).

It is also possible in an analogous manner to remove other cell populations, such as tumor cells, from the bone marrow, which is of importance for so-called autologous bone marrow transplantation (see in this connection Kvalheim et al., Cancer Research (1987), 47, 846–851 and the literature cited therein). This can also entail, as described by Kvalheim et al., ibid., the monoclonal antibody which recognizes the tumor cells being directly bound to the magnetic particles so that the above-mentioned second antibody (rabbit anti-mouse) is no longer required.

The method, described above, of bone marrow depletion using monoclonal or polyclonal antibodies which are bound to magnetic particles is still very new and requires further development and testing. Magnetic particles suitable for this purpose are now commercially available in a wide variety of forms and the preparation thereof has been described several times in the patent literature (see, for example, Chagnon et al., EP 0125995 A2 (priority U.S. Pat. No. 493991 of May 12, 1983), Advanced Magnetics, or Ughelstad et al., WO 8303920 of Nov. 10, 1983, SINTEF). It is known of these magnetic particles that they are composed of a metal oxide core in which paramagnetic substances can be embedded, and that the core is surrounded by an enveloping coat which can carry reactive groups such as, for example, aminophenyl, amino, carboxyl, hydroxyl or sulfhydryl groups which can be used for coupling proteins (Chagnon et al., EP 0125995 A2).

It is known, for example, that particles carrying carboxyl groups can be reacted with amino groups of proteins in the presence of a condensing agent (Chagnon et al., EP 0125995 A2).

It is furthermore known to couple proteins to magnetic particles carrying amino groups by use of glutaraldehyde, in which case the coupling takes place via the amino groups in each case (Chagnon et al., EP 0125995 A2).

It is additionally known that particles carrying hydroxyl groups can be activated by reaction with p-toluenesulfonyl chloride and that particles activated in this way can be reacted with amino groups of proteins (Kvalheim et al., Cancer Research (1987), 47, 846-851).

It is common to all these coupling methods that the protein is attached to the particles in each case via its free amino groups. However, such coupling via amino groups can be a considerable disadvantage with monoclonal antibodies because this occasionally impairs the specificity and reactivity of the antibodies. This is a consequence of the fact that the amino groups in an antibody are, as it were, randomly distributed over the entire molecule and thus also located in the antigen-binding site of the Fab fragments, which brings about a loss of specificity on coupling via these amino groups.

It is additionally known that antibodies can also be picked up on magnetic particles purely by adsorption, without any chemical linkage, when the particles are composed of a styrene/divinylbenzene copolymer which contains iron oxide, because it is known that protein binds non-specifically to polystyrene.

However, impairment of the antibody specificity and reactivity must be expected with this method, too. Another serious disadvantage of this method is that, however, antibodies bound by adsorption become detached again on bone marrow depletion and thus may also be administered to the patient on reinfusion of the depleted bone marrow, which might lead to serious side effects, especially where there has been previous attempted therapy with monoclonal antibodies. However, this problem is known and is to be overcome by covalent attachment of the antibodies to the magnetic particles.

It is also known that polystyrene-based magnetic particles have the serious disadvantage that they tend to aggregate and, moreover, attach themselves non-specifically to cells.

Starting from this state of the art, the object of the present invention is to develop a method in which monoclonal antibodies are coupled to magnetic particles a) covalently and b) not via their amino groups. Hence, in other words, the object of the present invention is to find a coupling method in which the antigen-binding site of the antibody is not altered or the coupling of the antibody takes place away from the antigen-binding site.

This object according to the invention is achieved by preparing magnetic protein conjugates of the formula I.

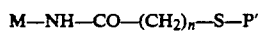

M—NH—CO—(CH$_2$)$_n$—S—P'   I

It has already been proposed to convert magnetic particles carrying amino groups into magnetic particles which carry as reactive groups maleimido functionalities, and to conjugate the latter with proteins which have sulfhydryl groups, it being possible for the sulfhydryl groups in the protein to be either already present naturally or introduced by chemical means or generated by reduction of disulfide linkages which are present.

It has now been found that magnetic particles which carry free amino groups as reactive groups can also be converted straightforwardly into magnetic particles which carry iodoacetyl or bromoacetyl functionalities as reactive groups. Particles of this type are new.

It has additionally been found that magnetic particles which carry iodoacetyl or bromoacetyl functionalities can be conjugated without difficulty to proteins which have sulfhydryl groups, it being possible for the sulfhydryl groups in the protein either to be already naturally present or introduced by chemical means or generated by reduction of disulfide linkages which are present.

It has been found, in particular, that magnetic particles which carry iodoacetyl or bromoacetyl functionalities can be conjugated without difficulty to monoclonal antibodies when the interchain disulfide linkages of the antibodies are converted by selective reduction into free SH groups which can be induced to react with the iodoacetyl or bromoacetyl functionalities of the magnetic particles with the formation of a thioether linkage. This mode of coupling monoclonal antibodies to magnetic particles is likewise new.

It has been found, surprisingly, that the specificity and reactivity of the antibodies coupled via thioether linkages to magnetic particles is completely retained because the coupling of the antibody via its hinge region means that there is no alteration or impairment of its antigen-binding site. This is responsible for a particular advantage of the invention compared with hitherto disclosed coupling methods in which the antibodies are, as described above, picked up on magnetic particles either purely by adsorption or via reaction of their amino groups, which may impair both the specificity and the reactivity of the conjugated antibodies. Moreover, the present invention has the advantage compared with coupling by adsorption that the antibodies are chemically bonded to the magnetic particles, and, as a consequence, are not detached from the particles on use of magnetic antibody conjugates according to the invention, for example for bone marrow depletion.

It has additionally been found that the non-specific adsorption of antibodies onto the magnetic particles which takes place occasionally can be prevented or reversed by addition of a suitable detergent.

It has additionally been found that the magnetic antibody conjugates according to the invention prove to be particularly advantageous, because of their high specificity, in the depletion of bone marrow, for example.

It has additionally been found that the magnetic antibody conjugates according to the invention also prove to be advantageous, because of their high specificity, as part of a diagnostic method or as a diagnostic aid, in particular, for example, in HLA typing.

The preparation of magnetic antibody conjugates according to the invention is described by way of example hereinafter for various monoclonal antibodies which are directed against cells of the bone marrow and for a polyclonal rabbit immunoglobulin; however, the said examples do not restrict the invention. In addition, the use of the prepared examples of magnetic antibody conjugates for the depletion of cells of the bone marrow is likewise described by way of example, without restricting the use to the said examples.

Process for the preparation of magnetic protein conjugates of the formula I

Magnetic particles M which carry amino groups are reacted in a suitable solvent with a halogenoacyl spacer compound which reacts with amino groups and has the formula II

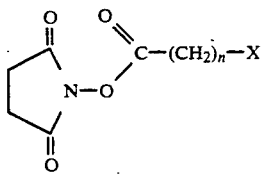

in which n=1 or 2 and X is a chlorine, bromine or iodine atom, with the formation of an amide linkage to give a compound of the formula III $$M-NH-CO-(CH_2)_n-X \qquad III$$

which is finally reacted in a suitable aqueous salt-containing solvent which does not denature proteins, such as, for example, physiological saline solution or a phosphate-buffered saline solution, with a protein P carrying sulfhydryl groups, to give a compound of the formula I, after which the resulting compound of the formula I is washed free of any non-covalently bonded protein which is present with the addition of a suitable detergent such as, for example, Tween.

Solvents suitable for the coupling of a compound of the formula II to magnetic particles must be of such a constitution that there is no impairment of the physical and magnetic properties of the magnetic particles used in each case for the coupling, in particular of the size, dispersibility and surface characteristics thereof, by the solvent which is used. An example of a solvent suitable for magnetic particles as are described, for example, in EP 0125995 A2 or WO 8303920 has been found to be a mixture of water and dimethylformamide.

Determination of the degree of coupling (μg of antibody/mg of iron)

Iron was determined by atomic absorption and nitrogen by the Kjeldahl method. The values for the coupled protein nitrogen were calculated by the formula $$\frac{\mu g\ P\text{-}N}{mg\ Fe} = \frac{\mu g\ \text{Tot-N}}{mg\ Fe}\ (\text{sample}) - \frac{\mu g\ \text{Tot-N}}{mg\ Fe}\ (\text{control})$$

where the terms have the following meaning:
P'-N: protein nitrogen
Tot-N.: total nitrogen
Fe: iron The amount of protein bound to the particles (μg of protein/mg of iron) was calculated from the amount of protein nitrogen per mg of iron by multiplication by the factor 6.25. The calculated coupling rates are compiled in Table 1.

Method for depletion of cells

A suspension of a cell mixture which is to be depleted in a salt-containing, preferably physiological aqueous solution or in a body fluid is incubated with a compound of the formula I at a suitable temperature between, for example, 0° C. and 40° C., preferably with shaking, likewise preferably under sterile conditions, for a suitable period, and then the magnetic particles are removed from the solution by a suitable magnet.

Examples of suitable temperatures are 0° C., room temperature or 37° C., but room temperature is preferred. The duration of the incubation depends in each case on the incubation temperature used and on the binding reactivity of the antibody and can be, for example, from a few minutes up to, for example, two hours. Incubation is preferably at, for example, room temperature for a period of, for example, 10 to 20 minutes.

Method for the isolation of soluble bioorganic molecules

This method essentially follows the method for depletion of cells.

EXAMPLES

The examples which follow serve to illustrate the invention in detail, but do not restrict the invention.

Magnetic particles which have been reacted with monoclonal antibodies in the manner described are called "magnetobeads" hereinafter, with their specificity being indicated in each case by prefixing the particular antibody name.

Example 1

Conjugation of magnetic particles disclosed in EP 0125995 A2 with N-hydroxysuccinimidyl iodoacetate 4×300 μl of a commercially available suspension of magnetic particles (BioMag ®, Advanced Magnetics) were each washed 3× with 10 ml of phosphate-buffered saline solution, pH 7.2, (PBS) each time and each were resuspended in 3 ml of PBS. To each of these suspensions was added a freshly prepared solution of 10 mg of N-hydroxysuccinimidyl iodoacetate (NHIA; Rector et al., J. Immunol. Meth. (1978), 24, 321-336) in 2 ml of dry dimethylformamide in each case, and the mixtures were shaken at room temperature for 1 h. The particles were then removed by centrifugation at 3,000×g, washed in each case 3× with 10 ml of PBS each time and resuspended in a) 5 ml, b) 4.3 ml, c) 3.6 ml and d) 2.9 ml of PBS pH 7.2.

Example 2

Conjugation of magnetic particles disclosed in EP 0125995 A2 with N-hydroxysuccinimidyl bromoacetate Conjugation was carried out in analogy to Example 1 with N-hydroxysuccinimidyl bromoacetate (NHBrA), the NHBrA being prepared in analogy to the preparation of NHIA by the method of Rector et al., ibid.

Example 3

Coupling of polyclonal rabbit anti-mouse immunoglobulin (RAM) to particles activated as in Example 1

3 mg of polyclonal rabbit anti-mouse immunoglobulin in phosphate-buffered saline solution (500 μl) were mixed with 3 mg of dithiothreitol and incubated at room temperature for 30 min. The reduced antibody was isolated by gel filtration through Sephadex G25 in phosphate-buffered saline solution, pH 7.2, in an elution volume of 4.2 ml and added to the particle suspensions a-d prepared as in Example 1, as follows:
a: no addition (control)
b: addition of 0.7 ml (about 0.5 mg of protein)
c: addition of 1.4 ml (about 1.0 mg of protein)
d: addition of 2.1 ml (about 1.5 mg of protein)

The mixtures (5 ml each) were each incubated with shaking at room temperature for 1 h. The particles were then removed by centrifugation at 3,000×g, washed 3× with 10 ml of PBS each time, resuspended in 5 ml of PBS pH 7.2, and stored at 4° C. The analytical data are compiled in Table 1.

Example 4

Coupling of polyclonal rabbit anti-mouse immunoglobulin (RAM) to particles activated as in Example 2.

Coupling was carried out in analogy to Example 3. The analytical data are compiled in Table 1.

Example 5

Coupling of the monoclonal antibody BMA 081 (anti-CD8; IgG2a) to particles activated as in Example 1

2 mg of BMA 081 in PBS (500 μl) were mixed with 1 mg of dithiothreitol and incubated at room temperature for 30 min. The reduced antibody was isolated by gel filtration through Sephadex G25 in phosphate-buffered saline solution, pH 7.2, in an elution volume of 3.6 ml and added to the particle suspensions a–d prepared as in Example 1, as follows:

a: no addition (control)
b: addition of 0.4 ml (about 0.2 mg of protein)
c: addition of 1.2 ml (about 0.6 mg of protein)
d: addition of 2.0 ml (about 1.0 mg of protein)

The mixtures (about 5 ml each) were each incubated with shaking at room temperature for 1 h. The particles were then removed by centrifugation at 3,000×g, washed 3× with 10 ml of PBS each time, resuspended in 5 ml of PBS pH 7.2, and stored at 4° C. The analytical data are compiled in Table 1.

Example 6

Coupling of the monoclonal antibody BMA 0110 (anti-CD2; IgG2b) to particles activated a in Example 1

The coupling was carried out in analogy to Example 5. The analytical data are compiled in Table 1.

Example 7

Depletion of CD8+ cells from mononuclear cells using magnetobeads prepared as in Example 5

Mononuclear cells (MNC) were isolated from freshly donated human blood in a manner known per se (Boyum, Scand. J. Immunol. (1976), Suppl. 5, 9–15) on a Ficoll gradient.

For the depletion, $3 \times 10^7$ MNC in 2 ml of PBS containing 1% BSA (w/v, Seromed) in plastic tubes (Falcon, No. 2051) were mixed with 1 ml of a suspension of 2 mg/ml magnetobeads in PBS and incubated at room temperature, shaking continuously, for 15 min. The magnetobeads prepared as in Example 5 and the cells bound thereto were then removed using a permanent magnet. The cells remaining in suspension were pelleted at 400×g and resuspended in a suitable medium, for example PBS or RPMI 1640. The depletion efficiency was determined by indirect immunofluorescence in a cytofluorograph (Ortho).

For this purpose, $1 \times 10^6$ cells were, before and after depletion of a defined cell population, labeled with 1 μg/ml first antibody BMA 031 (Behringwerke AG) and then with 20 μg/ml second antibody (rabbit anti-mouse immunoglobulin, F(ab)2 fragment, FITC-labeled, Behringwerke) in a manner known per se and evaluated in a cytofluorograph, where the depletion efficiency was determined to be above 95%.

TABLE 1

Degrees of coupling of various prepared magnetobeads

| Example | Antibody | Isotype | Coupling method | Coupling ratio Protein/iron (μg/mg) |
|---------|----------|---------|-----------------|-------------------------------------|
| 3b | RAM | poly | NHIA | 74 |
| 3c | RAM | poly | NHIA | 136 |
| 3d | RAM | poly | NHIA | 171 |
| 4b | RAM | poly | NHBrA | 98 |
| 4c | RAM | poly | NHBrA | 143 |
| 4d | RAM | poly | NHBrA | 167 |
| 5b | BMA 081 | IgG2a | NHIA | 56 |
| 5c | BMA 081 | IgG2a | NHIA | 107 |
| 5d | BMA 081 | IgG2a | NHIA | 113 |
| 6b | BMA 0110 | IgG2b | NHIA | 76 |
| 6c | BMA 0110 | IgG2b | NHIA | 156 |
| 6d | BMA 0110 | IgG2b | NHIA | 183 |

RAM: rabbit anti-mouse immunoglobulin
poly: polyclonal
NHIA: N-hydroxysuccinimidyl iodoacetate
NHBrA: N-hydroxysuccinimidyl bromoacetate

We claim:
1. A magnetic protein conjugate of the formula I

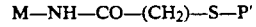

$$M-NH-CO-(CH_2)-S-P' \qquad I$$

in which M is a dispersible particle with a metal oxide core and an enveloping coat carrying amino groups, and P' is a protein, wherein the diameter of the particle is between about 0.1 micron and about 100 micron.

2. A magnetic protein conjugate as claimed in claim 1, wherein the sulfhydryl group or sulfhydryl groups of the protein P' are either present in the natural way or generated by reduction of disulfide linkages or introduced by chemical reaction into the protein.

3. A magnetic protein conjugate as claimed in claim 1, wherein P' is a polyclonal immunoglobulin.

4. A magnetic protein conjugate as claimed in claim 1, wherein P' is a monoclonal antibody or a Fab, Fab' or F(ab')2 fragment.

5. A magnetic protein conjugate as claimed in claim 1, wherein P' is a monoclonal antibody of the IgG or IgM class.

6. A magnetic protein conjugate as claimed in claim 1, wherein P' is a monoclonal antibody which is directed against an antigen which is present in dissolved form in aqueous salt solutions or body fluids.

7. A magnetic protein conjugate as claimed in claim 1, wherein P' is a monoclonal antibody which is directed against an antigen which is expressed on cells 8. A magnetic protein conjugate as claimed in claim 1, wherein P' is a monoclonal antibody which is directed against an antigen which is expressed on bacteria, mycoplasmas, protozoa or viruses.

9. A magnetic protein conjugate as claimed in claim 7, wherein said cells are of the myeliod or lymphatic system or of the peripheral blood.

10. A magnetic protein conjugate as claimed in claim 9, wherein said cells are selected from B lymphocytes, T lymphocytes, the precursor cells thereof and tumor cells.

11. A magnetic protein conjugate as claimed in claim 10, wherein said cells are tumor cells of the bone marrow.

12. A magnetic protein conjugate as claimed in claim 11, wherein a group of paramagnetic substances is embedded in the metal oxide core.

13. A magnetic protein conjugate as claimed in claim 2, wherein the sulfhydryl group or sulfhydryl groups of the protein P are generated by reduction of disulfide linkages.

14. A process for the preparation of a magnetic protein conjugate of the formula I, M—NH—CO—(CH$_2$)$_n$—S—P'   I which comprises magnetic particles M which carry amino groups being reacted with a halogenoacyl spacer which reacts with amino groups and has the formula II

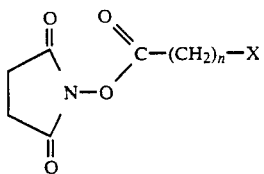

wherein X is a chlorine, bromine or iodine atom, with the formation of an amide linkage to give a compound of the formula III M—NH—CO—(CH$_2$)—X III which is finally reacted with a protein P' carrying sulfhydryl groups to give a compound of the formula I, after which the resulting compound of the formula I is washed free of non-covalently bonded protein.

15. The process of claim 14, wherein the sulfhydryl groups are generated by reduction of disulfide linkages.

* * * * *